United States Patent [19]
Dorsey et al.

[11] Patent Number: 5,181,527
[45] Date of Patent: Jan. 26, 1993

[54] PROPHYLACTIC DEVICE

[76] Inventors: James C. Dorsey, 8328 46th Ave., SW., Seattle, Wash. 98136; Johnnie L. Moore, 11390 NE. 36th Pl., #A 137, Bellevue, Wash. 98004

[21] Appl. No.: 833,929

[22] Filed: Feb. 11, 1992

[51] Int. Cl.⁵ .............................................. A61F 5/42
[52] U.S. Cl. ...................... 128/830; 128/832; 128/842; 128/844
[58] Field of Search ............... 128/830, 832, 834–836, 128/842, 844; 604/342

[56] References Cited

U.S. PATENT DOCUMENTS

| | | | |
|---|---|---|---|
| 3,536,066 | 10/1970 | Ludwig | 128/830 |
| 4,393,871 | 7/1983 | Vorhauer et al. | |
| 4,664,104 | 5/1987 | Jaicks | 128/830 |
| 4,794,920 | 1/1989 | Robichaud | |
| 4,807,611 | 2/1989 | Johnson | |
| 4,834,113 | 5/1989 | Reddy | 128/830 |
| 4,862,901 | 9/1989 | Green | 128/830 |
| 4,898,184 | 2/1990 | Skurkovich | |
| 4,966,165 | 10/1990 | Anderson | 128/830 |
| 4,976,273 | 12/1990 | Hessel | |
| 4,993,431 | 2/1991 | Reddy | 128/830 |
| 4,993,433 | 2/1991 | Reddy | |
| 5,076,287 | 12/1991 | Johnson | |

FOREIGN PATENT DOCUMENTS

| | | | |
|---|---|---|---|
| 3723458 | 1/1989 | Fed. Rep. of Germany | 128/830 |
| 2649316 | 1/1991 | France | 128/830 |

*Primary Examiner*—Robert A. Hafer
*Assistant Examiner*—Kerry Owens
*Attorney, Agent, or Firm*—Graybeal Jackson Haley & Johnson

[57] ABSTRACT

A prophylactic device has a first band adapted to be worn around the waist of a human female and a second band connected to the first band and adapted to be worn between the buttocks of a human female such that the anus is covered by the second band. A genitalia shield connects the first band and the second band and covers the perineum of the human female. The genitalia shield portion includes a sheath having an open integral therewith. The sheath is stored in a retracted position in which its length is diminished by a plurality of folded pleats. Placement of a member against the opening of the sheath unfolds the pleats to orient the sheath in an extended position such that the sheath enters the vaginal opening and is oriented within the vagina. Removable tabs attached to the genitalia shield portion and oriented over both sides of the sheath retain lubricant and/or spermicide adjacent to the two sheath sides.

11 Claims, 2 Drawing Sheets

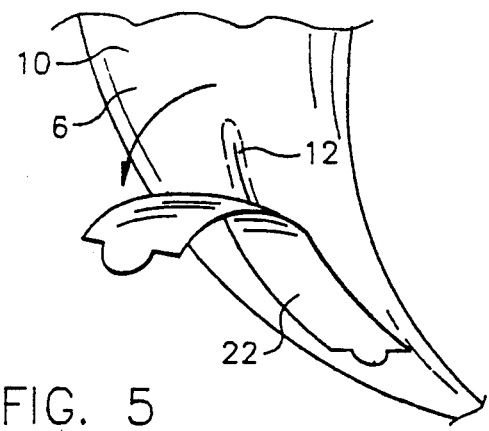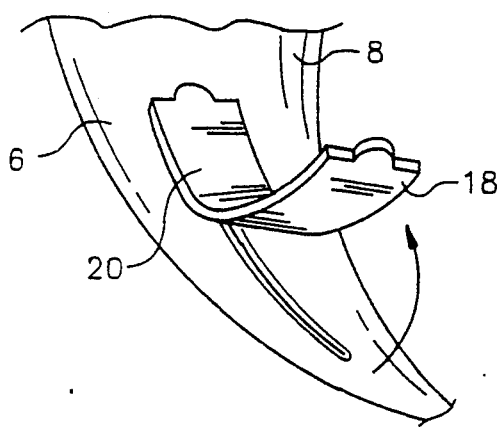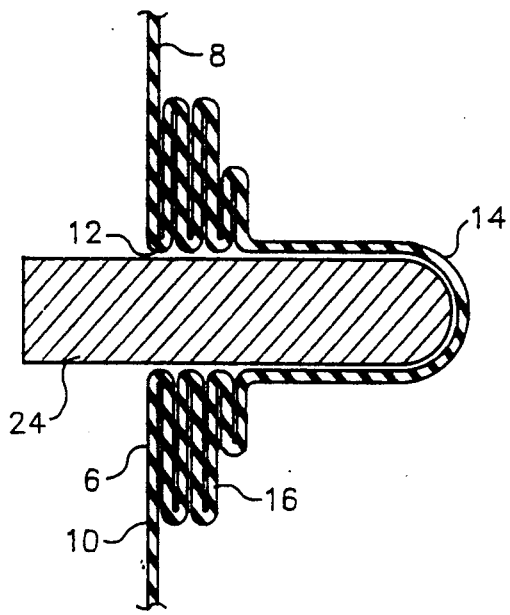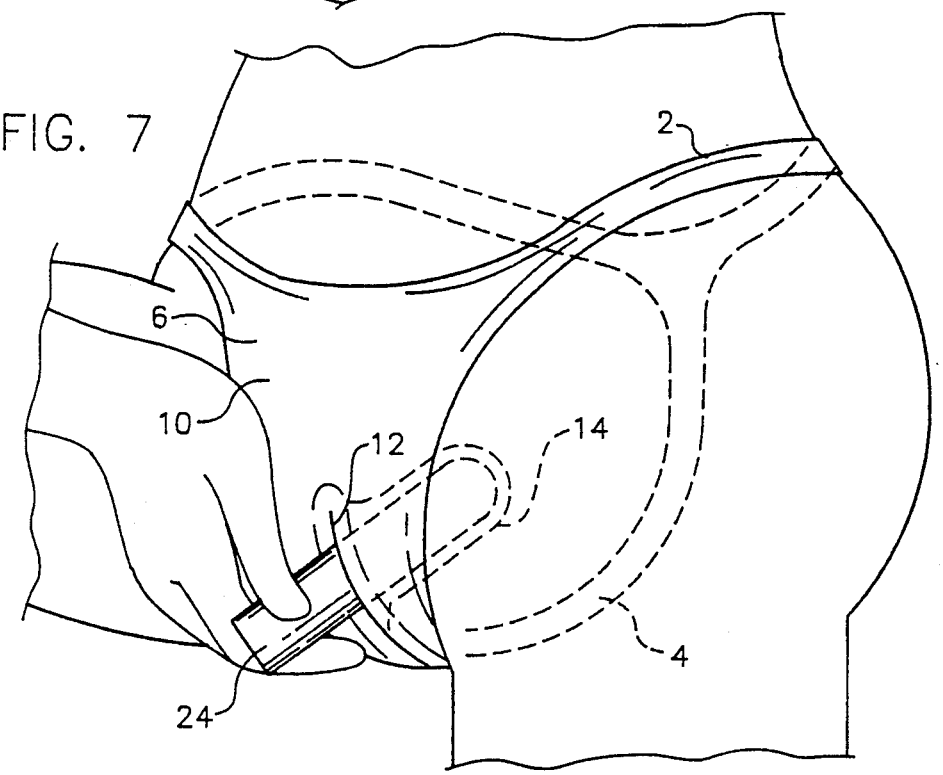

PROPHYLACTIC DEVICE

BACKGROUND OF THE INVENTION

The prophylactic device of the present invention pertains to birth control and disease prevention, and more particularly to devices designed to prevent the spread of sexually transmitted disease.

Acquired Immune Deficiency Syndrome (AIDS) is caused by a virus, known as HIV, that attacks the body's mechanism for fighting infections, i.e., the immune system. AIDS is contracted from an infected person by passage of the virus in bodily fluid, such as semen or blood, through a break in the skin of a person who is, for example, having sexual relations with the infected person. A break in the skin in the perineum is a common transmission point of the AIDS virus. The perineum area is defined as the diamond shaped portion of the body lying between the thighs and bounded at the posterior by the coccyx, or tailbone, anteriorly by the pubic bone, and laterally by the pair of ischial tuberosities. This area is frequently subject to pimples, skin infection, rashes or the like; and is very likely to be contacted by semen absent prophylactic efforts.

The most common method for prevention of sexually transmitted diseases such as AIDS is the use of condoms. However, condoms only cover the penis, thus leaving uncovered the vulnerable perineum. Additionally, spillage of semen from a condom often occurs, and leakage onto the perineum is the frequent result.

Prior art patents exist which disclose prophylactic devices that cover portions of the perineum, but leave the anus exposed. Additionally, none of the prior art devices are intended to be worn by a female for an extended period of time prior to intercourse. The inability of these devices to be worn for a significant time prior to intercourse is due to the bulky components and uncomfortable fit of the devices. Specifically, U.S. Pat. No. 4,993,433 issued to Reddy discloses a prophylactic device which includes an elongated hollow pouch which has an opening and a closed end. The pouch has a thin wall member which is flexible and elastic. A continuous flange member is attached to the open end of the pouch and extends outwardly around the opening in the pouch. Attachment straps secured to the flange attach the device to the person wearing it.

U.S. Pat. No. 4,993,431, issued to Reddy, teaches a prophylactic device with a planar portion that is configured to cover the perineum of the user. The planar portion includes a pair of spaced, integrally formed, adjustably positionable thigh bands located in spaced parallelism on either side of the planar portion. A leg opening is formed between each of the thigh bands and the planar portion to accommodate the legs of the user. The bands elastically shape to the user to prevent slippage of the planar portion from the perineum of a user. The planar portion includes a pouch of generally circular cross-section throughout its length for insertion into a bodily orifice.

U.S. Pat. No. 4,898,184 issued to Skurkovich, et al. discloses a condom device having an apron portion for covering the pubic area, thigh portion for covering the perineum and genitalia portions. Straps integral with the condom, or adhesives, are used to hold the condom in place.

While other prior art patents do disclose prophylactic devices which cover the anus, these devices are also not intended to be worn for an extended time prior to intercourse due to their uncomfortable fit and bulky design. Specifically, U.S. Pat. No. 4,807,661 issued to Johnson teaches a prophylactic device having a body portion fitting the wearer like a garment, extending from the vicinity of the navel downward to extend under the thighs. A trap portion, either integral with or fixed to the body portion, covers the perineum of the wearer. The trap portion is formed of a highly expandable material and fitted loosely. The trap portion can respond to pressure from within or without to extend outwardly or inwardly to maintain an impermeable barrier between a penetrating member and the interior of a target orifice.

U.S. Pat. No. 4,966,165 issued to Anderson discloses a unisex condom to be worn as an underpant type garment with pocket or shaft type depressions or tubular extensions in the lower front and lower rear. During use the tubular extensions can be inserted inside the lower body cavities such as the vagina and anus. Alternatively, the tubular extensions can be reversed or turned inside out or placement as a covering or exterior liner for a penis.

A major factor in the efficacy of a prophylactic device is the convenience of use of said device. If a prophylactic device is not convenient to use it will not be use. A primary reason that individuals shun prophylactic devices, such as the above disclosed prior art devices, is that they must be donned immediately prior to intercourse because they are uncomfortable and unsightly to wear for long periods of time beforehand. Putting on a prophylactic device immediately prior to intercourse is undesirable because, not only is it distracting, but unintentional exchange of bodily fluid can occur prior to or during donning of the prophylactic device.

A need thus exists for a prophylactic device which is configured to cover the perineum of the user including not only the genitals but the anus as well.

A need exists for the above type of prophylactic device which is configured to be comfortable and nonobtrusive such that it can be worn for an extended period of time prior to intercourse.

A need exists for the above type of prophylactic device which is unobtrusive when not in use due to the low-profile storage of the sheath portion of the device.

A need exists for the above type of prophylactic device which is comfortable to wear for an extended period of time prior to intercourse because moisture absorbent material is present on the portion of the device contacting the female external genitalia.

A need exists for the above type of prophylactic device in which spermicide and/or a lubricant can be stored adjacent both sides of the retracted sheath prior to use of the device, and in which removal of adhesively secured tabs frees the condom and the spermicide and/or lubricant for use during sexual intercourse.

SUMMARY OF THE INVENTION

In accordance with the present invention a prophylactic device for preventing the exchange of bodily fluids is formed of an elastic impermeable material and is adapted to be worn by a human female. The prophylactic device includes a first band adapted to be worn around the waist, and a second band connected to the first band and adapted to be worn between the buttocks such that the anus is covered by the second band. A genitalia shield portion connected to the first band and the second band covers the perineum of the female wearer and includes a sheath having an opening integral with the genitalia shield portion. The sheath is stored in a retracted position in which its length is diminished by a plurality of folded pleats. The sheath is adapted to be oriented adjacent to the vaginal opening of the wearer when in this retracted position. The sheath also has an extended position in which the length of the sheath is increased by placing a member against the sheath opening to unfold the pleats such that the sheath enters the vaginal opening and is oriented within the vagina.

A removable inner sealing tab covers the sheath when it is in the retracted position. The removable inner sealing tab is adhesively secured to the inner side of the genitalia shield portion and retains lubricant and/or spermicide adjacent to the side of the sheath which contacts the vagina. The removable inner sealing tab includes a layer of absorbent material thereon substantially in plane with the genitalia shield portion, and functions as a panty shield to facilitate long term wearing of the prophylactic device a considerable period of time prior to sexual intercourse.

A removable outer sealing tab covers the opening of the sheath when the sheath is in its retracted position. The removable outer sealing tab is adhesively secured to the outer side of the genitalia shield to retain lubricant and/or spermicide within the sheath.

With the sheath in the retracted position, the prophylactic device of the subject invention can be worn by a female for an extended period of time prior to intercourse. When intercourse is imminent, the removable inner sealing tab and removable outer sealing tab are separated from the genitalia shield portion of the prophylactic device and the sheath is configured from its retracted position into its extended position by placing a member against the opening of the sheath to unfold the pleats thereof such that the sheath enters the vaginal opening and is oriented within the vagina. In its extended position, the sheath has a length and a diameter greater than the length and diameter of an erect penis such that the penis can move relative to the sheath during sexual intercourse.

BRIEF DESCRIPTION OF THE DRAWINGS

These and other features of the present invention will be evident when considered in light of the following specification and drawings in which:

FIG. 4 is a detailed view of the removable outer tab of the prophylactic device of the present invention;

FIG. 5 is a detailed view of the removable inner tab of the prophylactic device of the present invention;

FIG. 6 is a detailed side view of the sheath of the prophylactic device of the present invention in its pleated, retracted position; and FIG. 7 is a perspective view of the prophylactic device of the present invention in which the sheath is being oriented in its extended position by the female wearer.

DETAILED DESCRIPTION OF THE PREFERRED EMBODIMENT

Figure 1:
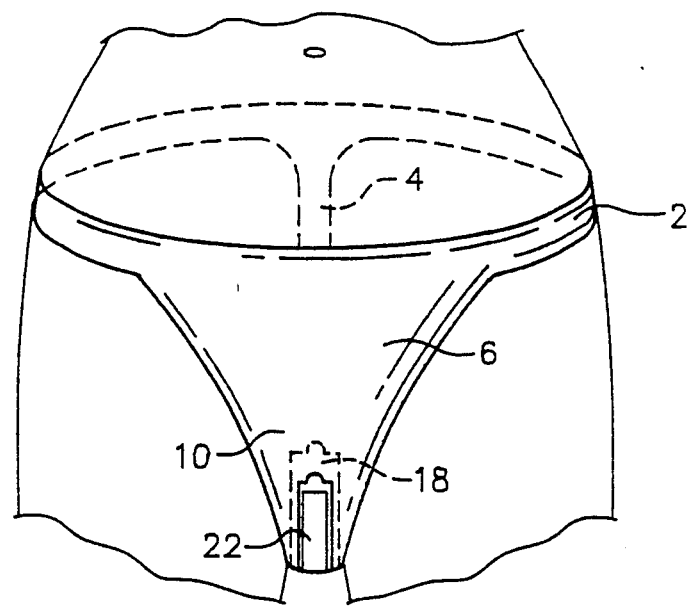
FIG. 1 is a front perspective view of the prophylactic device of the present invention while being worn by a human female.
Figure 2:
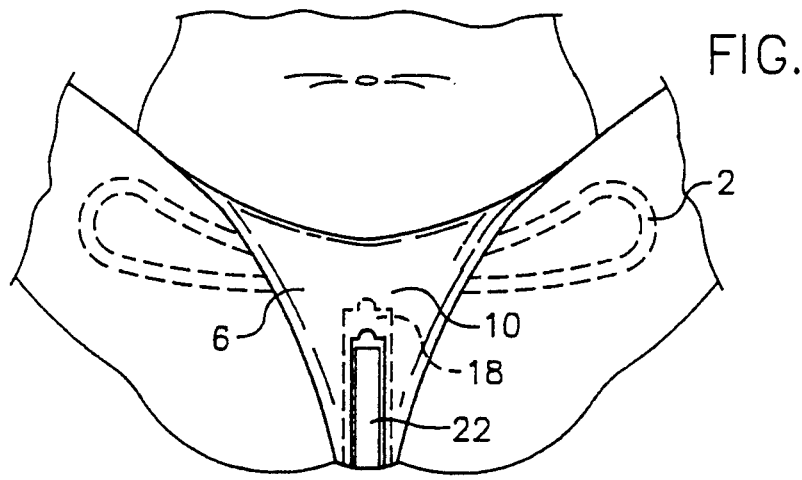
FIG. 2 is another front perspective view of the prophylactic device of the present invention while being worn by a human female.
Figure 3:
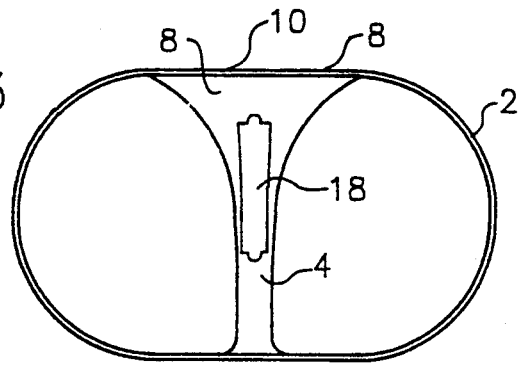
FIG. 3 is a top view of the prophylactic device of the present invention.

Referring to FIGS. 1-7, the prophylactic device of the present invention is preferably comprised of a flexible and elastic material, such as rubber which may be natural or synthetic. Synthetic materials such as polyurethane, polyvinylchloride, or a silicon elastomer may be employed. The prophylactic device includes a first band 2 adapted to be worn around the waist of a human female. A second band 4 is connected to first band 2 at the rear portion thereof and is adapted to be worn between the buttocks of the human female such that the anus of the human female is covered by the second band 4. The end of second band 4 not connected to first band 2 is connected to genitalia shield 6 which is sized and shaped to cover the perineum of the human female. The end of genitalia shield 6 not connected to second band 4 is connected to first band 2 at the front portion thereof, thus forming a prophylactic device substantially having a G-string configuration. While this G-string configuration is preferred, it is apparent that, optionally, the buttocks of the human female may be covered by additional, flexible and elastic material connected to the rear of first band and to second band 4 (not shown). Preferably, first band 2, second band 4 and genitalia shield 6 are integrally formed; however, one or more of these elements may be separate components which are joined to the others in a manner known in the art such as by adhesives or thermal bonding.

Genitalia shield 6 has an inner side 8 which fits snugly against the perineum and genitals of the human female, and an outer side 10. Genitalia shield 6 also has an opening 12 which is preferably slit-shaped. Opening 2 is located in the center of genitalia shield 6 such that when the prophylactic device of the present invention is worn by a human female, opening 12 is oriented over, and in alignment with, the vaginal opening of the female. Opening 12 of genitalia shield 6 defines sheath 14 of genitalia shield 6, sheath 14 being integrally connected to genitalia shield 6. Sheath 14 has a penile side communicating with opening 12 and outer side 10 of genitalia shield 6, and a vaginal side communicating with inner side 8 of genitalia shield 6.

The prophylactic device of the present invention may be worn by a human female for an extended time period prior to sexual intercourse, such as, for example, numerous hours. In order for the prophylactic device of the present invention to be comfortable and form-fitting prior to its use during intercourse, sheath 14 is stored in a retracted position in which the length of sheath 14 is diminished by folding sheath 14 against the inner side of genitalia shield 6 such that a plurality of pleats 16 are present. The pleated folding of sheath 14 thus allows storage of sheath 14 in its retracted position in a manner which minimizes the cross-sectional profile of sheath 14, thus resulting in a less bulky and more comfortable prophylactic device than such devices which roll the sheath for storage.

Removable inner sealing tab 18, preferably affixed to inner side 8 of genitalia shield 6 with an adhesive or other suitable means of fastening, is oriented over sheath 14 to retain sheath 14 in its retracted position. The pocket so formed by removable inner sealing tab 18 and inner side 8 of genitalia shield 6 preferably contains lubricants and/or spermicides (e.g., such as the spermicide commercially available under the name "NONOXONAL 9") adjacent to sheath 14 when stored in its retracted position. Removable inner sealing tab 18 is preferably comprised of a liquid resistant polymer, or paper coated with a liquid-resistant polymer, known in the art. Most preferably, the side of removable inner sealing tab 18 in plane with inner side 8 of genitalia shield 6 includes a layer of absorbent material 20 which is preferably a padding of cotton or synthetic fiber commonly employed in panti shields or the like. Absorbent material 20 thus increases the comfort while wearing the prophylactic device of the present invention for a substantial period of time because absorbent material 20 not only functions as a traditional panti shield but provides a layer of soft padding between genitalia shield 6 and the sensitive female external genitalia.

Removable outer sealing tab 22, preferably affixed to outer side 10 of genitalia shield 6 with an adhesive or other suitable means of fastening, is oriented over opening 12 of sheath 14. The pocket so formed by removable outer sealing tab 22 and outer side 10 of genitalia shield 6 preferably contains the above described lubricant and/or spermicide within opening 12 of sheath 14 when stored in its retracted position. Removable outer sealing tab 22 is preferably comprised of a liquid-resistant polymer, or paper coated with a liquid-resistant polymer, known in the art. Thus, the combination of removable inner sealing tab 18 and removable outer sealing tab 22 allows storage of lubricant and/or spermicide adjacent to the vaginal side and the penile side, respectively, of sheath 14 when stored.

When sexual intercourse is imminent, removable sealing tab 18 and removable outer sealing tab 22 are removed from genitalia shield 6. A piloting member 24 is placed against opening 12 of sheath 14 to orient sheath 14 in its extended position by unfolding pleats 16 thereof such that sheath 14 enters the vaginal opening of the human female and is oriented within the vagina. Thus, sheath 14 preferably forms a loose fitting cover of the walls of the vaginal cavity and has a length and diameter greater than the length and diameter of an erect penis such that the penis can move relative to said sheath during sexual intercourse. After sexual intercourse is completed, the prophylactic device of the present invention is discarded.

While particular embodiments of the present invention have been described in some detail herein above, changes and modifications may be made in the illustrated embodiments without departing from the spirit of the invention.

We claim:

1. A prophylactic device for preventing the exchange of bodily fluids, formed of elastic impermeable material, and adapted to be worn by a human female comprising:
    a first band portion adapted to be worn around the waist of a human female;
    a second band portion connected to said first band portion, said second band portion adapted to be worn between the buttocks of a human female such that the anus of the human female is covered by said second band portion;
    a genitalia shield portion connected to said first band portion and said second band portion, said genitalia shield portion having an inner side and an outer side, said genitalia shield portion adapted to cover the perineum of a human female, said genitalia shield portion including a sheath having an opening integral with said genitalia shield portion, said sheath having a retracted position in which the length of said sheath is diminished, said sheath adapted to be oriented adjacent to the vaginal opening of a human female when in said retracted position, said sheath having an extended position in which the length of said sheath is increased by placing a member against said opening of said sheath such that said sheath enters the vaginal opening of a human female and is oriented within the vagina; and
    a removable inner sealing means covering said sheath when said sheath is in said retracted position, said removable inner sealing means secured to said inner side of said genitalia shield portion to retain at least one of lubricant and spermicide adjacent the vaginal side of said sheath.

2. The prophylactic device of claim 1 wherein said sheath has a vaginal side and a penile side, said genitalia shield portion further comprising:
    a removable outer sealing means covering said opening of said sheath when said sheath is in said retracted position, said removable outer sealing means secured to said outer side of said genitalia shield portion to retain at least one of lubricant and spermicide within said penile side of said sheath whereby said removable outer sealing means and said removable inner sealing means are removed from said genitalia shield portion to orient said sheath in said extended position for sexual intercourse.

3. The prophylactic device of claim 1, said removable inner sealing means further comprises:
    a layer of absorbent material on said removable inner sealing means substantially in plane with said interior side of said genitalia shield portion.

4. The prophylactic device of claim 2 wherein said removable inner sealing means and said removable outer sealing means are tabs adhesively secured to said genitalia shield portion.

5. The prophylactic device of claim 1 wherein said sheath has a length and a diameter greater than the length and the diameter of an erect penis when said sheath is oriented in said extended position such that the penis can move relative to said sheath during sexual intercourse.

6. A prophylactic device for preventing the exchange of bodily fluids, formed of elastic impermeable material, and adapted to be worn by a human female comprising:
    a first band portion adapted to be worn around the waist of a human female;
    a second band portion connected to said first band portion, said second band portion adapted to be worn between the buttocks of a human female such that the anus of the human female is covered by said second band portion; and
    a genitalia shield portion connected to said first band portion and said second band portion, said genitalia shield portion having an inner side and an outer side, said genitalia shield portion adapted to cover the perineum of a human female, said genitalia shield portion having:
        a sheath having an opening integral with said genitalia shield portion, having a vaginal side, and having a penile side, said sheath having a retracted position in which the length of said sheath is diminished, said sheath adapted to be oriented adjacent to the vaginal opening of a human female when in said retracted position, said sheath having an extended position in which the length of said sheath is increased by placing a member against said opening of said sheath to extend said sheath such that said sheath enters the vaginal opening of a human female and is oriented within the vagina, a removable inner sealing means covering said sheath when said sheath is in said retracted position, said removable inner sealing means secured to said inner side of said genitalia shield portion to retain at least one of lubricant and spermicide adjacent said vaginal side of said sheath, and a removable outer sealing means covering said opening of said sheath when said sheath is in said retracted position, said removable outer sealing means secured to said outer side of said genitalia shield portion to retain at least one of lubricant and spermicide within said penile side of said sheath whereby said removable outer sealing means and said removable inner sealing means are removed from said genitalia shield portion to orient said sheath in said extended position for sexual intercourse.

7. The prophylactic device of claim 6 wherein the length of said sheath when in said retracted position is diminished by a plurality of folded pleats, and the length of said sheath is increased by placing a member against said opening of said sheath to unfold said pleats.

8. The prophylactic device of claim 6, said removable inner sealing means further comprising:

a layer of absorbent material on said removable inner sealing means substantially in plane with said interior side of said genitalia shield portion.

9. The prophylactic device of claim 6 wherein said removable inner sealing means and said removable outer sealing means are tabs adhesively secured to said genitalia shield portion.

10. The prophylactic device of claim 6 wherein said sheath has a length and a diameter greater than the length and the diameter of an erect penis when said sheath is oriented in said extended position such that the penis can move relative to said sheath during sexual intercourse.

11. A prophylactic device for preventing the exchange of bodily fluids, formed of elastic impermeable material, and adapted to be worn by a human female comprising:

a first band portion adapted to be worn around the waist of a human female;

a second band portion connected to said first band portion, said second band portion adapted to be worn between the buttocks of a human female such that the anus of the human female is covered by said second band portion; and a genitalia shield portion connected to said first band on and said second band portion, said genitalia shield portion having an inner side and an outer side, said genitalia shield portion adapted to cover the perineum of a human female, said genitalia shield portion having;

a sheath having an opening integral with said genitalia shield portion, having a vaginal side, and having a penile side, said sheath having a retracted position in which the length of said sheath is diminished by a plurality of folded pleats, said sheath adapted to be oriented adjacent to the vaginal opening of a human female when in said retracted position, said sheath having an extended position in which the length of said sheath is increased by placing a member against said opening of said sheath to unfold said pleats such that said sheath enters the vaginal opening of a human female and is oriented within the vagina, a removable inner sealing means covering said sheath when said sheath is in said retracted position, said removable inner sealing means secured to said inner side of said genitalia shield portion to retain at least one of lubricant and spermicide adjacent said vaginal side of said sheath, said removable inner sealing means including a layer of absorbent material thereon substantially in plane with said interior side of said genitalia shield portion, and a removable outer sealing means covering said opening of said sheath when said sheath is in said retracted position, said removable outer sealing means secured to said outer side of said genitalia shield portion to retain at least one of lubricant and spermicide within said penile side of said sheath whereby said removable outer sealing means and said removable inner sealing means are removed from said genitalia shield portion to orient said sheath in said extended position for sexual intercourse.

* * * * *